United States Patent [19]

Durrum et al.

[11] Patent Number: 4,861,866
[45] Date of Patent: Aug. 29, 1989

[54] CONTINUOUS FLOW PEPTIDE SYNTHESIZER

[75] Inventors: Emmett L. Durrum, Menlo Park; Stephen Amendola, San Carlos, both of Calif.; Bruce W. Erickson, Chapel Hill, N.C.

[73] Assignee: Eldex Laboratories, Inc., Menlo Park, Calif.

[21] Appl. No.: 5,915

[22] Filed: Jan. 21, 1987

[51] Int. Cl.[4] .................. C12M 1/00; C12M 1/36; A61K 37/02; C07C 103/52
[52] U.S. Cl. .................. 530/333; 530/334; 422/134; 422/188; 525/54.11
[58] Field of Search ........... 530/333, 334; 422/134, 422/188; 525/54.1, 54.11

[56] References Cited

U.S. PATENT DOCUMENTS

| | | | |
|---|---|---|---|
| 4,065,412 | 12/1977 | Dreyer | 525/54.1 |
| 4,130,514 | 10/1978 | Enkoji et al. | 530/334 |
| 4,192,798 | 3/1980 | Verlander et al. | 525/54.11 |
| 4,362,699 | 12/1982 | Verlander et al. | 530/334 |
| 4,517,338 | 5/1985 | Urdea et al. | 525/54.11 |
| 4,598,049 | 7/1986 | Zelinka et al. | 525/54.11 |

Primary Examiner—John Kight
Assistant Examiner—Nathan M. Nutter
Attorney, Agent, or Firm—Flehr, Hohbach, Test, Albritton & Herbert

[57] ABSTRACT

A continuous flow peptide synthesizer (10) has reservoirs (12-42) for amino acid derivatives and reservoirs (154-156 and 161-167) for peptide synthesis reagents and solvents. A column (44) has column segments (224, 226, 228) forming stacked interconnected chambers for holding peptide synthesis polymeric resin supports (260). Each of the amino acid derivative reservoirs (12-42) and the reagent and solvent reservoirs (152-154 and 161-167) are connected through a separate controllable valve (46-76, 154-156 or 182-194) to the column (44). A pressurized source (106) of helium or other inert gas is provided for transferring the amino acid derivatives, reagents and solvents to the column (44). The column segments (224) are also used in a vessel (270) for confining the polymeric resin supports (260) in the vessel during cleavage of the peptides from the supports (260).

24 Claims, 5 Drawing Sheets

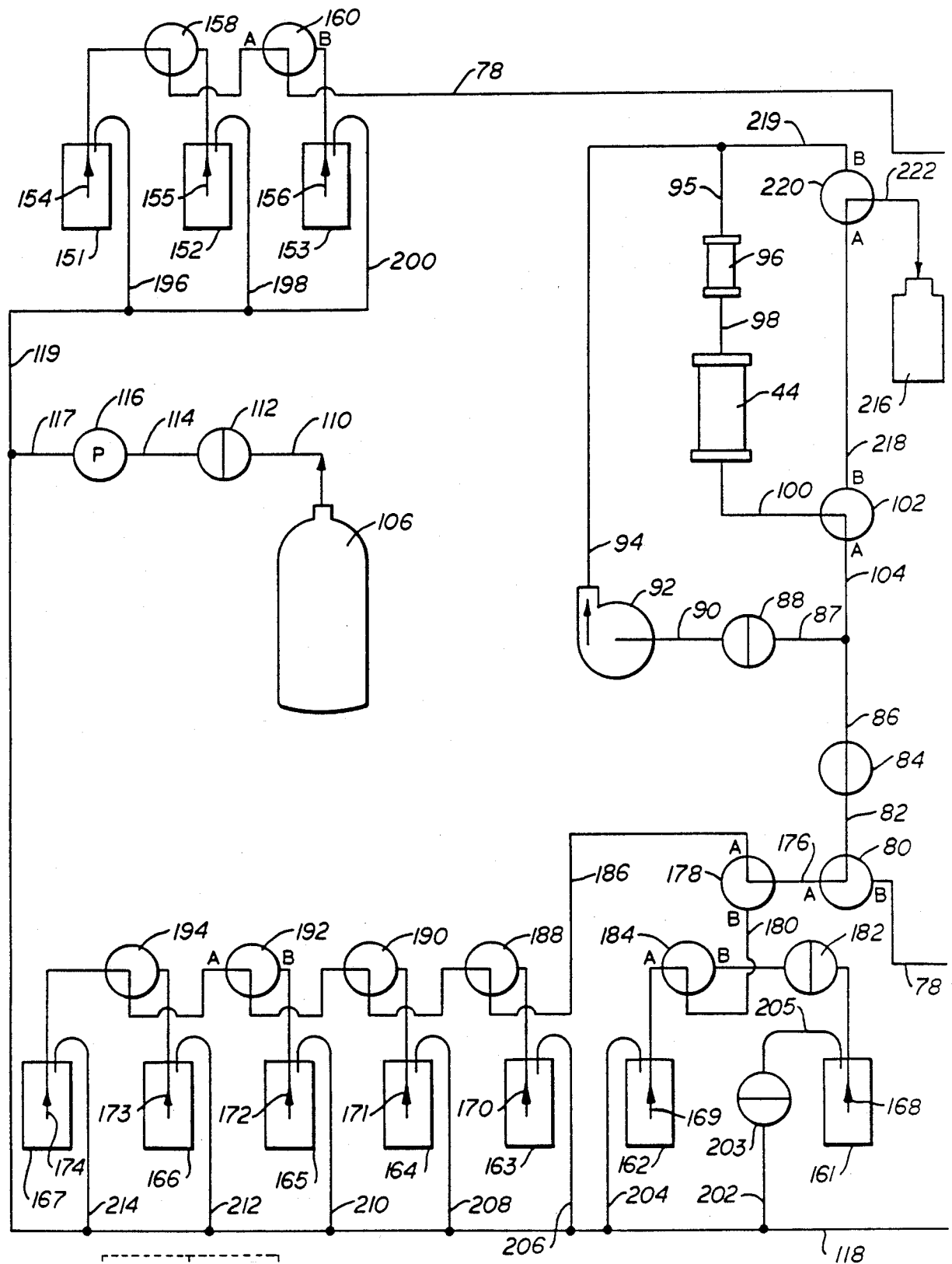
FIG._1A.

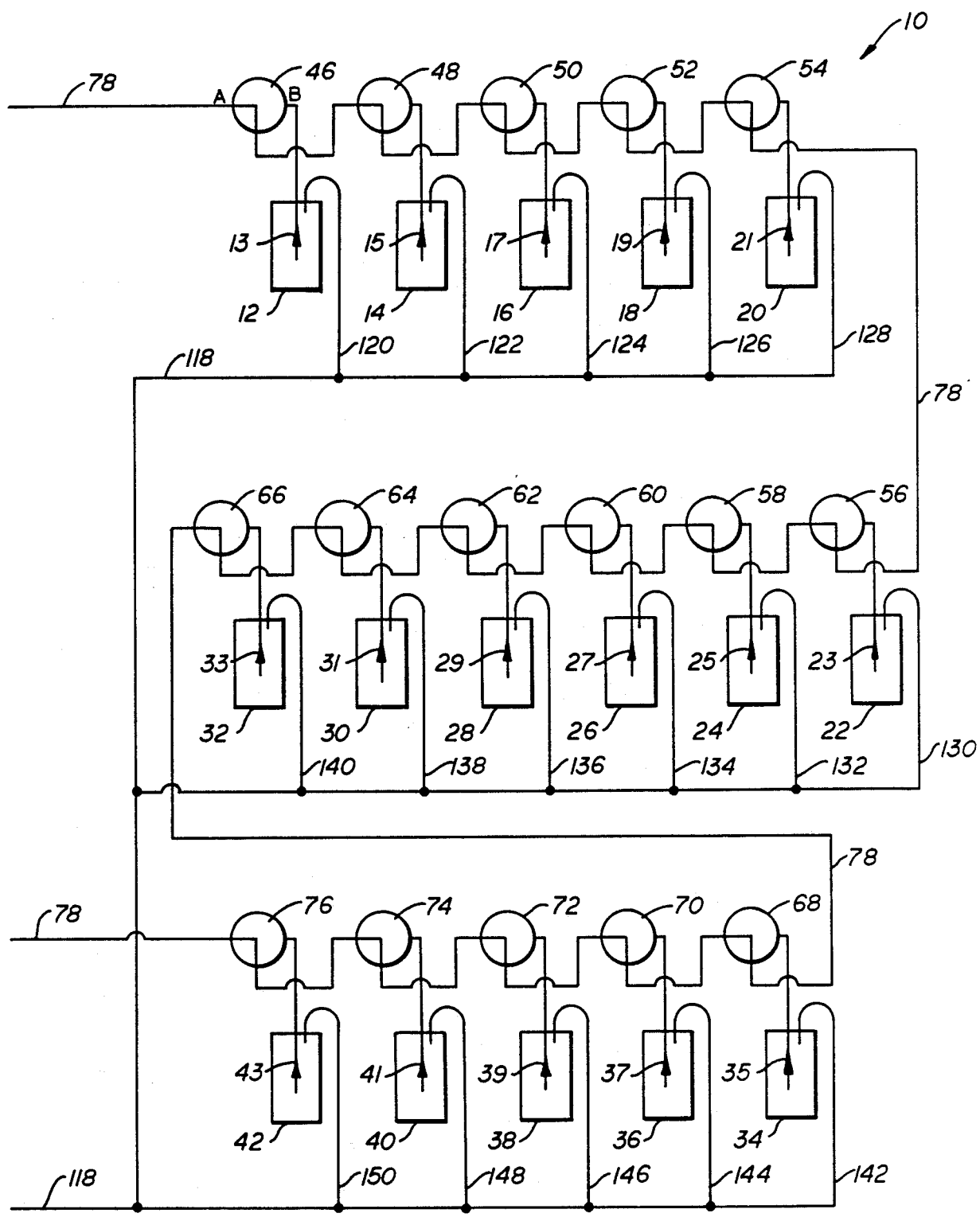
FIG._1B.

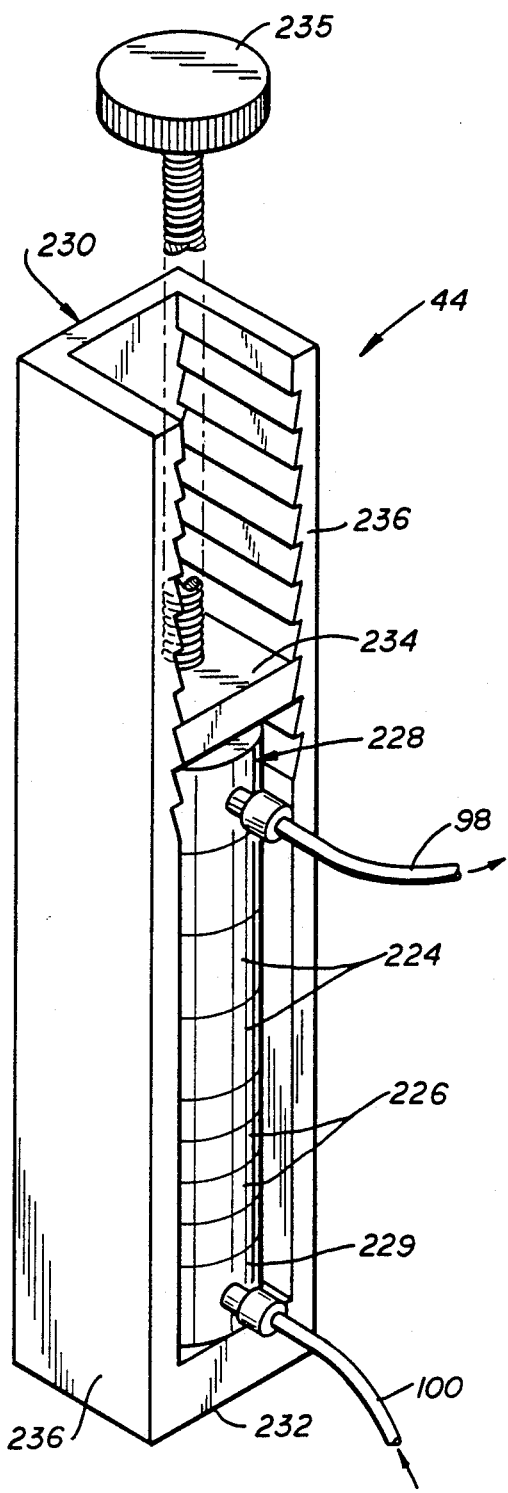
FIG._2.
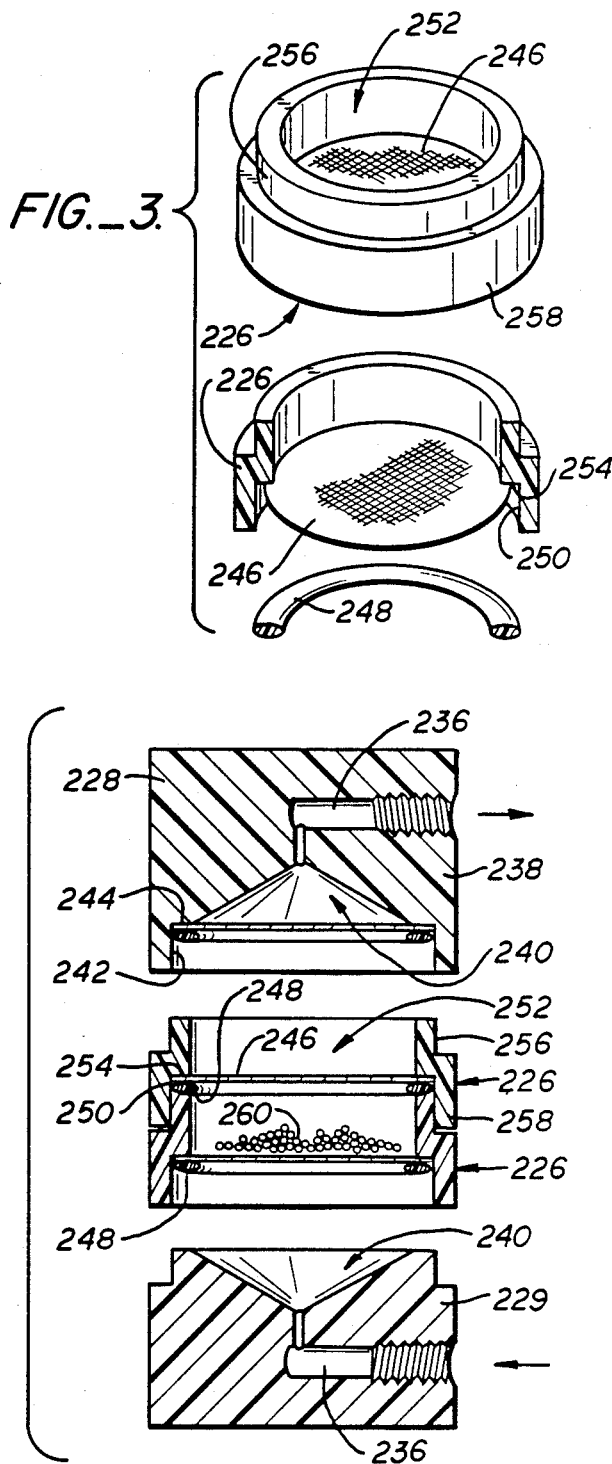
FIG._3.
FIG._4.

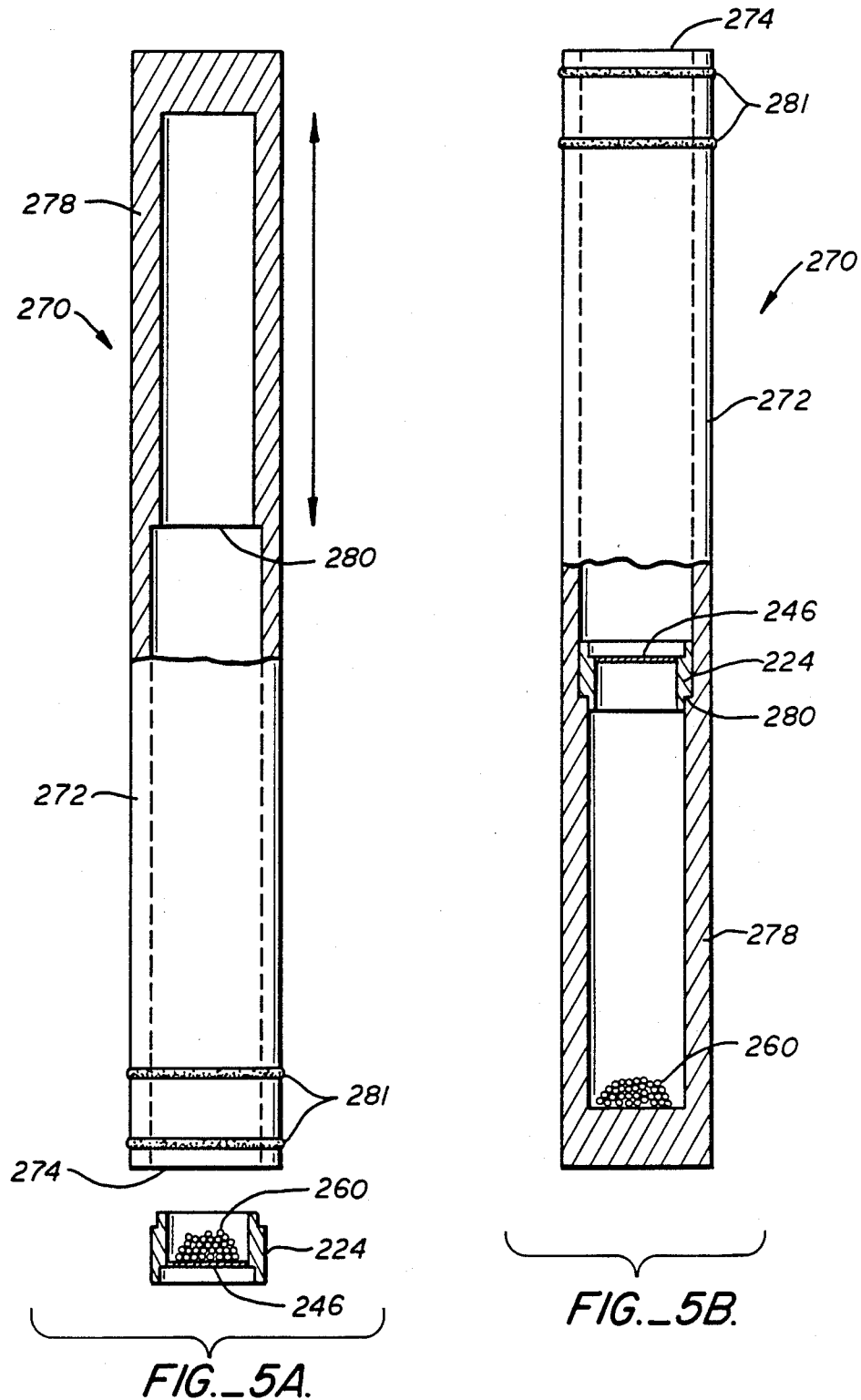
FIG._5A.
FIG._5B.

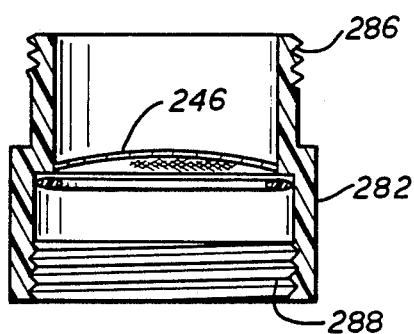
FIG._6.
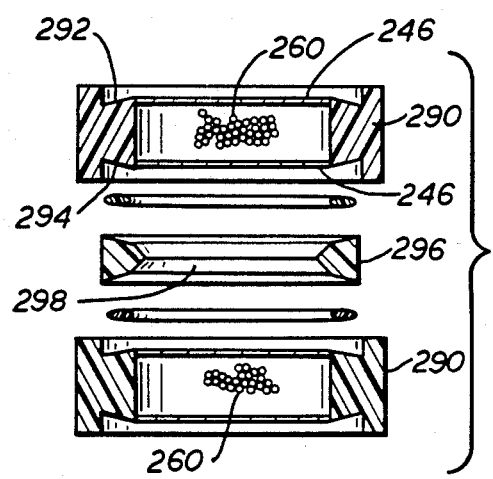
FIG._7.
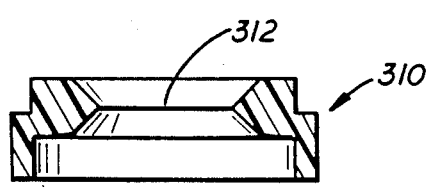
FIG._9.
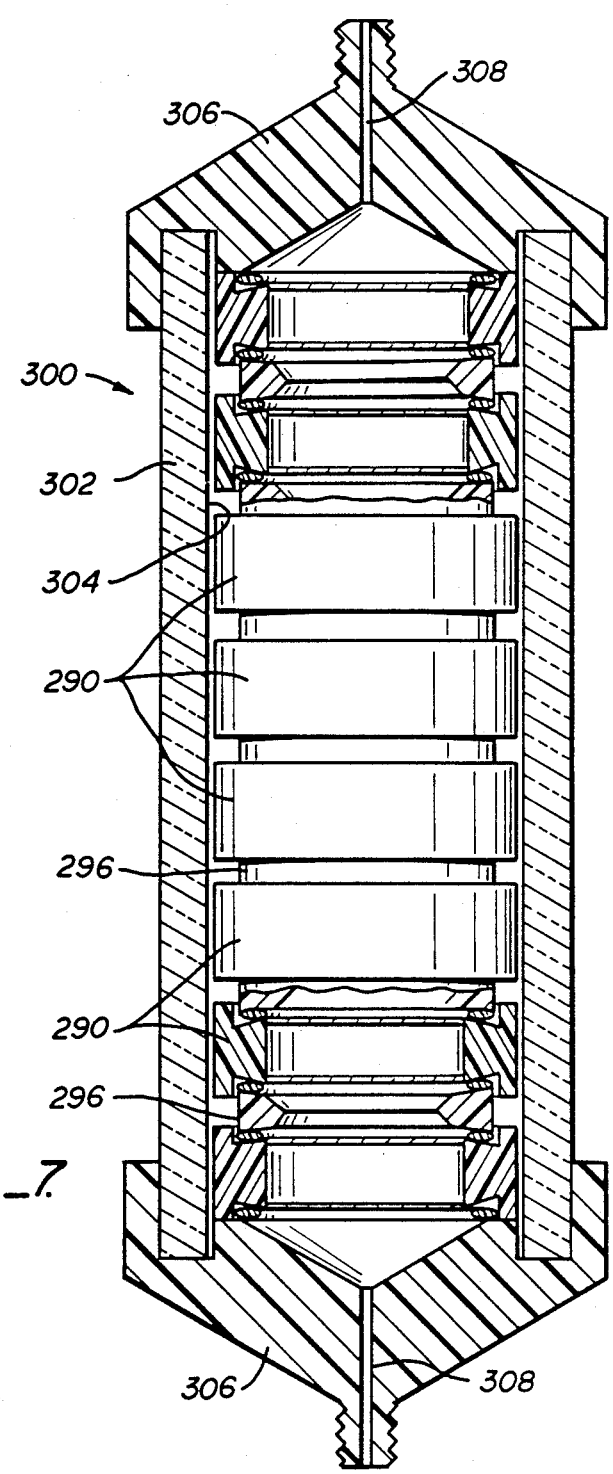
FIG._8.

CONTINUOUS FLOW PEPTIDE SYNTHESIZER

BACKGROUND OF THE INVENTION

1. Field of the Invention

This invention relates to an improved continuous flow peptide synthesizer system and column for use in such a system. It also relates to an improved column segment for use in the column and the system. The invention further relates to an improved continuous flow peptide synthesis process which may be carried out using the synthesizer, column and column segment. The invention also relates to an improved hydrogen fluoride-resin cleavage system incorporating the column segments.

2. Description of the Prior Art

The state of the art in the synthesis of many different peptides concurrently and multiple-analog peptide synthesis is summarized by Richard A. Houghten, "General method for the rapid solid-phase synthesis of large numbers of peptides: Specificity of antigen-antibody interaction at the level of individual amino acids," Proc. Natl. Acad. Sci. USA, Vol. 82, pp. 5131–5135, August 1985. In the method described there, starting resin is placed in polypropylene mesh packets, and process steps which are the same for all of the peptides to be synthesized are carried out on the packets simultaneously as a group. While this method permits the synthesis of larger numbers of peptides in a more cost efficient manner and in a shorter period of time per peptide, further efficiencies would be possible with equipment and a process sequence more amenable to continuous flow methods.

SUMMARY OF THE INVENTION

Accordingly, it is an object of this invention to provide a continuous flow peptide synthesizer in which a number of different peptides or a number of analogs of a particular peptide may be produced concurrently.

It is another object of the invention to provide such a continuous flow peptide synthesizer in which resins on which the different peptides or analogs are synthesized may be assembled in stacked relationship for their concurrent production.

It is a further object of the invention to provide an improved column particularly adapted for use in a continuous flow peptide synthesizer.

It is still another object of the invention to provide an improved column segment for stacking resins on which different peptides or analogs are concurrently produced in a column.

It is yet another object of the invention to provide an improved peptide synthesis process in which continuous reagent flows are employed.

It is still another object of the invention to provide an improved hydrogen fluoride-resin cleavage vessel incorporating the column segments.

The attainment of these and related objects may be achieved through use of the novel continuous flow peptide sythesizer, column, column segment and continuous flow peptide synthesis process herein disclosed. A continuous flow peptide synthesizer in accordance with this invention has a first plurality of reservoirs for amino acid derivatives and a second plurality of reservoirs for peptide synthesis reagents. A column having a third plurality of column segments forms stacked interconnected chambers for holding peptide synthesis polymeric resin supports. Each of the first plurality of amino acid reservoirs and the second plurality of reagent reservoirs are connected through a separate controllable valve to the column. A means is provided for supplying the amino acid derivatives and the reagents to the column.

A peptide synthesis column in accordance with the invention has a housing configured to support a plurality of column segments in stacked relationship to form an interconnected plurality of stacked chambers. The housing has at least one member movable along its length to allow the housing to support a variable number of the column segments in the stacked relationship. The plurality of column segments include an inlet column segment, an outlet column segment and at least one additional column segment between the inlet column segment and the outlet column segment.

A column segment in accordance with the invention is formed by a cylinder having an axially extending bore with a mesh screen extending across the axially extending bore. The cylinder is configured to mate with a like cylinder in stacking relationship to form interconnected stacked chambers defined by the mesh screen in adjacent column segments when the column segments are assembled in stacked relationship.

A continuous flow peptide synthesis process in accordance with the invention includes providing a plurality of peptide synthesis polymeric resin support bodies stacked in a column, flowing peptide synthesis reagents for a plurality of synthesis steps which are identical for the plurality of resin support bodies through the stacked bodies in the column, separating the stacked bodies for at least one synthesis step which is different for the resin support bodies, and flowing at least one different peptide synthesis reagent for each separated resin support body through the separated resin support bodies. The at least one separated synthesis step may come at any point in the plurality of identical synthesis steps.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is a key showing placement of FIGS. 1A and 1B.

FIGS. 1A and 1B are a schematic and block diagram of a continuous flow peptide synthesizer in accordance with the invention.

FIG. 2 is a perspective view of a column in accordance with the invention for use with the synthesizer of FIG. 1.

FIGS. 3 and 4 are enlarged perspective and cross section views of column segments in accordance with the invention for use with the column of FIG. 2.

FIGS. 5A and 5B are side views of an vessel for gas cleavage utilizing the column segments of FIG. 3.

FIG. 6 is a side view of another embodiment of a column segment in accordance with the invention.

FIG. 7 is a side view of a third embodiment of a column segment in accordance with the invention.

FIG. 8 is a side cross section view of a second embodiment of a column in accordance with the invention.

FIG. 9 is a side cross section view of an insert usable with the FIGS. 2–4 embodiment of the invention.

DETAILED DESCRIPTION OF THE INVENTION

Turning now to the drawings, more particularly to FIGS. 1A and 1B, there is shown a continuous flow peptide synthesizer 10 in accordance with the invention. The synthesizer 10 has a plurality of reservoirs 12-42 for solutions of amino acid derivatives to be transferred to a functionalized polymeric resin support, hereafter resin, present within column 44. The amino acid derivatives commonly used are N-(tert-butoxycarbonyl) amino acids or N-(9-fluorenylmethoxycarbonyl) amino acids. When amino acid derivatives are mentioned below, it is to be understood that these aforementioned amino acid derivatives and other less commonly employed amino acid derivatives can be used. Reservoirs 12-42 containing amino acid derivative solutions are connected to column 44 by means of reservoir outlets 13-43, line 78 through valves 46-76, valve 80, line 82, valve 84, lines 86 and 87, valve 88, line 90, pump 92, lines 94 and 95, bubble trap 96 and line 98. Alternatively, line 86 is connected to column 44 by line 104, valve 102, and line 100. In order to supply gas pressure for transferring an amino acid derivative solution into line 78 and towards column 44, a source 106 of helium or other inert gas under pressure is connected by line 110, valve 112, line 114, pressure regulator 116, line 117 and line 118 to inlets 120-150 of the amino acid derivative reservoirs 12-42. Solvent reservoirs 151-153 are connected to the column 44 by outlets 154-156, valves 158 and 160, line 78 through valves 46-76, valve 80, line 82, valve 84, lines 86 and 87, valve 88, line 90, pump 92, lines 94 and 95, bubble trap 96, and line 98. Reagent and additional solvent reservoirs 161-167 are connected to column 44 by outlets 168-174, either line 186 through valves 188-194 or line 180 through valves 182 and 184, valve 178, line 176, valve 80, line 82, valve 84, lines 86 and 104, valve 102 and line 100. In order to supply gas pressure for transferring the reagents and solvents through their respective reservoir outlets and towards column 44, pressurized gas source 106 is connected by line 110, valve 112, line 114, pressure regulator 116, line 77, and thence through line 119 to inlets 151-153 of reservoirs 154-156, through lines 118 and 202 and valve 203 to inlet 205 of reservoir 168, and through line 118 to inlets 204-214 of reservoirs 162-167.

Line 86 is connected to waste reservoir 216 in three modes. In the prime mode, the liquid flow proceeds from line 86 through line 87, valve 88, line 90, pump 92, lines 94 and 219, valve 220, and line 222 to waste reservoir 216. In the flush mode, the liquid flow proceeds from line 86 through line 104, valve 102, line 100, column 44, line 98, bubble trap 96, lines 95 and 219, valve 220, and line 222 to waste reservoir 216. In the pump mode, the liquid flow proceeds from line 86 through line 87, valve 88, line 90, pump 92, lines 94 and 95, bubble trap 96, line 98, column 44, line 100, valve 102, line 218, valve 220 and line 222 to waste reservoir 216. In addition, once the desired liquids have been pumped during the pump mode into the system between lines 87 and 100, a fourth mode called the cycle mode can be started by closing valve 84 and switching valve 102 to connect lines 100 and 104, so that the liquid flow proceeds in a closed circle from line 87 through valve 88, line 90, pump 92, lines 94 and 95, bubble trap 96, line 98, column 44, line 100, valve 102, line 104, and back to line 87.

FIGS. 2, 3 and 4 show details of the column 44 and column segments 224, 226, 228 and 229 used in the column 44. The column 44 has a housing 230 with a fixed bottom 232 and a top 234 slideably movable along sides 236 toward and away from the bottom 232 to accomodate a greater or lesser number of the column segments 224, 226, 228 and 229 in the column 44. A thumbscrew 235 is threadably attached to the top 234 for applying clamping force on the segments 224, 226, 228 and 229 when they have been assembled in the column 44. The column segments 228 and 229 are used as an inlet and an outlet to the column 44. The segments 228 and 229 are hollow cylinders with a threaded, countersunk passage 237 extending from outside surface 238 to interior 240 of the segments 228 and 229. The interior 240 of the segment 228 has a portion 242 of greater inside diameter than the remainder of the interior, thus forming a ledge 244 around the portion 242. A mesh screen 246 attached to ring 248 rests against the ledge 244.

The segments 224 and 226 are spaced between the inlet and outlet segments 228 and 229 and are similar in construction to the segments 228. The only difference between the segments 224 and 226 is their height, which determines their interior capacity. The larger segments 224 are dimensioned to provide an interior capacity of, for example, 2 ml, and the smaller segments 226 are dimensioned to provide an interior capacity of 1 ml. The segments 224 and 226 also have a portion 250 of greater inside diameter than the remainder of their interior 252, to form ledge 254 against which the ring 248 of the mesh screen 246 rests. The segments 224 and 226 have a projecting portion 256 of their walls 258 which fits into the portion 250 or 242 of greater diameter of an adjacent segment 224, 226 or 228. In their assembled relationship in the column 44 as shown in FIG. 2, resin 260 (see also FIG. 4) is confined between the mesh screens 246 of adjacent segments 224, 226 and 228. With the larger segments 224, a quantity of 150 mg of the resin 260 is employed, to allow for a tenfold or more swelling during a peptide synthesis.

The segments 224, 226, 228 and 229, the screens 246 and the rings 248 may be fabricated from any material that is inert to the reagents employed in peptide synthesis. In practice, since anhydrous hydrofluoric acid is one of the reagents used, the segments 224, 226 and 228 are fabricated from polypropylene or other inert material, with ultrasonic welding of the screens 246 to the rings 248, both of which also are fabricated from polypropylene. Of course, other inert materials can be used for the screen 246 and the housing 230. The resin 260 is of the type conventionally employed in solid phase peptide synthesis, such as benzyl-linked polystyrene resins, spacer-linked styrene resins, polyamide resins or macroretricular resins.

In use of the system 10 for producing different peptides concurrently or to produce peptide analogs having single amino acid variations, the reaction steps for each of the peptides that use the same reagents are carried out together, with the segments 224, 226 and 228 stacked in the column 44. For those steps in which a different reagent is used for each peptide, the segments 224, 226 and 228 are separated from the stack and their resin 260 is treated separately with the different reagents in each case. The segments 224, 226 and 228 are then again stacked for common processing in additional steps with the same reagents. For example, a peptide 20 residues long with different amino acid analogs at the eighth residue may be fabricated by carrying out simultaneous processing in a column 44 for the first seven residues, the segments 224, 226 and 228 unstacked to separate the resin 260, the amino acids processed separately for the analogs at the eighth position, and the segments 224, 226 and 228 stacked in the column 44 for the remaining identical amino acids for each of the ninth through the twentieth positions.

In a specific example, the following table shows a program for double coupling of one N-(tert-butoxycarbonyl) amino acid, the double coupling constituting a known technique for increasing yield with the amino acid, and the double coupling as shown being used either for all of the resin support bodies in the column 44 or for a separated resin support body, depending on the peptides being synthesized:

TYPICAL PROGRAM FOR DOUBLE COUPLING OF ONE N—(TERT-BUTOXYCARBONYL) AMINO ACID

| | | | VALVE NUMBER = | | | | | | | | | | | | | | | | | |
|---|---|---|---|---|---|---|---|---|---|---|---|---|---|---|---|---|---|---|---|---|
| STEP | VESSEL | REAGENT | 112 | 160 | 203 | 182 | 184 | 192 | 178 | 80 | 84 | 88 | 102 | 220 | 46 | PUMP | TIME | FLOW | MODE |
| D1 | 161 | TFA | + | | | | | | B | | | | | B | | | 10:00 | UP | FLUSH |
| D2 | 167 | DCM | + | | | | | | | | | | | B | | | :29 | UP | FLUSH |
| D3 | 162 | ROH | + | | | | | | | | | | | B | | | :44 | UP | FLUSH |
| D4 | 167 | DCM | + | | | | | | | | | | | B | | | :29 | UP | FLUSH |
| N1 | 165 | DIEA | + | | | | | B | | | | | | B | | | 1:05 | UP | FLUSH |
| N2 | 167 | DCM | + | | | | | | | | | | | B | | | 1:24 | UP | FLUSH |
| C1 | 151 | DCM | + | | | | | | | | | | | | B | | 2:00 | NO | PRIME |
| C2 | 12 | AAD | | | | | | | | B | | + | B | | B | + | :13 | DOWN | PUMP |
| C3 | 153 | DIC | | B | | | | | | B | | + | B | | B | + | :13 | DOWN | PUMP |
| C4 | 151 | DCM | | | | | | | | B | | + | B | | B | + | :18 | DOWN | PUMP |
| C5 | | | | | | | | | | B | | + | B | | B | + | 30:00 | DOWN | CYCLE |
| C6 | 151 | DCM | + | | | | | | | B | | | | | B | | 3:00 | UP* | PU/FL |
| C7 | 151 | DCM | + | | | | | | | | | | | | B | | :39 | UP | FLUSH |
| C8 | 167 | DCM | + | | | | | | | | | | | B | | | :39 | UP | FLUSH |
| N1 | 165 | DIEA | + | | | | | B | | | | | | B | | | 1:05 | UP | FLUSH |
| N2 | 167 | DCM | + | | | | | | | | | | | B | | | 1:24 | UP | FLUSH |
| C1 | 151 | DCM | + | | | | | | | | | | | | B | | 2:00 | NO | PRIME |
| C2 | 12 | AAD | | | | | | | | B | | + | B | | B | + | :13 | DOWN | PUMP |
| C3 | 153 | DIC | | B | | | | | | B | | + | B | | B | + | :13 | DOWN | PUMP |
| C4 | 151 | DCM | | | | | | | | B | | + | B | | B | + | :18 | DOWN | PUMP |
| C5 | | | | | | | | | | B | | + | B | | B | + | 30:00 | DOWN | CYCLE |
| C6 | 151 | DCM | + | | | | | | | B | | | | | B | | 3:00 | UP* | PU/FL |
| C7 | 151 | DCM | + | | | | | | | | | | | | B | | :39 | UP | FLUSH |
| C8 | 167 | DCM | + | | | | | | | | | | | | B | | :39 | UP | FLUSH |

Abbreviations:
STEP: D = deprotection, N = neutralization, C = coupling;
REAGENT: TFA = trifluoroacetic acid, DCM = dichloromethane, ROH = isopropyl alcohol, DIEA = diisopropylethylamine, AAD = amino acid derivative (N—(tert-butoxycarbonyl) protection), DIC = diisopropylcarbonii-mide;
VALVE: blank = off or A state (as shown in FIG. 1), + or B = on or B state;
TIME: duration of step in min:sec;
FLOW: NO = no flow, UP* = up if gas flow rate is greater than pump flow rate;
MODE: PU/FL = combined pump and flush modes.

FIGS. 5A and 5B shows a vessel 270 in which the column segments 224 are used to confine the peptide carrying resin 260 in the vessel 270 during the use of anhydrous hydrogen fluoride to cleave the completed peptides from their carrying resin 260. The vessel 270 is formed from a column 272 having an open top 274 and a closed bottom 276. Wall 278 is thinner in its top section and thicker in its bottom section, defining a ledge 280. O-rings 281 below the top 274 allow the vessel 270 to be connected in a sealed manner to a commercially available HF peptide cleavage apparatus obtainable from Multiple Peptide Systems, La Jolla, Calif. 92038, under the designations #1024, #2010 and #3004. In FIG. 5A, the vessel 270 is inverted to allow insertion of the column segment 224 containing the resin 260 from which the peptide is to be cleaved. The segment 224 is pushed into the column 272 until it rests on the ledge 280. The vessel 270 is then reoriented with its top 274 facing upward, as shown in FIG. 5B. Column segment 224 and its screen 246 serve to confine the resin 260 within the lower half of the vessel 270 as fluids are introduced and removed through the top 274 of the vessel 270 during the peptide cleavage procedure. With the vessel in the position shown in FIG. 5B, the vessel 270 is tapped on a table to knock the resin to the bottom of the vessel 270. With the resin now trapped below the mesh 246 of the inverted segment 224, HF gas is condensed in the bottom of the vessel 270 in the usual way. The HF is distilled off under vacuum while the inverted segment 224 traps the resin 260 in the bottom of the vessel 270. This solves the serious problems of (1) foaming of the liquid HF as it is distilled off and (2) prevention of the resin 260 from being carried by the foam into distant parts of and apparatus including a number of the vessels 270, which usually causes contamination of other reaction vessels. In practice, except for the use of the vessel 270 and segment 224 as described, the cleavage procedure is carried out in the manner described in the instructions for using the above commercially available HF peptide cleavage apparatus. The vessel 270 both allows uniform reagent contact with the resin 260 and prevents expulsion of the resin 260 from the vessel 270 by the reagent fluids.

In use, the vessel 270 with the peptide carrying resin 260 in place is evacuated and chilled to $-70°$ C. A quantity of anhydrous hydrogen fluoride corresponding to 2 ml of HF per 100 milligrams of resin is supplied to the apparatus, and vacuum distillation is carried out, with stirring in an ice bath. The vessel 270 is usually kept at $0°$ C. for one hour. Aspiration is employed to remove the resulting gaseous HF, leaving the resin and free peptide. The free peptides are subsequently dissolved in dilute acetic acid or other suitable solvent.

FIG. 6 shows another form of column segment 282 that can be used in place of the column segments 224 and 226. The column segment 282 has mating threads 286 and 288 that are used to join the segments 282 with resin between the screens 246. In other respects, the construction and use of the FIG. 6 embodiment of the column segment is the same as in the FIGS. 2–4 embodiment.

In FIG. 7, the resin 260 is permanently maintained in segments 290 by a pair of screens 246 attached to top 292 and bottom 294 of each segment 290. The segments 290 are configured to be held in stacking registration by an insert 296, which is generally disk shaped, with a central orifice 298 extending through the disk for directing fluid flow between the segments 290. In practice, the segments 290 are supplied with the resin 260 prepackaged in them, ready for use.

FIG. 8 shows a column 300 in accordance with the invention, which consists of a glass tube 302 having an inside diameter sized to receive the segments 290. The glass tube 302 holds the stacked segments 290 in register, and the close fit between the inside wall 304 of the glass tube 302 and the segments 290 insures that most of the fluid flow between the segments 290 is through the orifices 298. End caps 306 on the tube 302 have central orifices 308 similar to the orifices 298 in the inserts 296.

FIG. 9 shows an insert 310 similar to the insert 296, but shaped for use with the FIGS. 2–4 embodiment. The insert 310 has a flow directing central orifice 312 serving the same function of directing reagent flow to the resin as the central orifice 298 in the insert 296.

It should now be readily apparent to those skilled in the art that a novel continuous flow peptide synthesizer, column, column segment and process capable of achieving the stated objects of the invention has been provided. The system and process of this invention allows a number of different peptides of a number of analogs of a particular peptide to be produced concurrently in a column. The novel column and column segment resins for such concurrent synthesis to be stacked for easy concurrent production. The column segments are also usuable in a vessel for supplying and removing hydrogen fluoride or other reagent gas for the resins and peptides.

It should further be apparent to those skilled in the art that various changes in form and detail of the invention as shown and described may be made. It is intended that such changes be included within the spirit and scope of the claims appended hereto.

What is claimed is:

1. A continuous flow peptide synthesizer, which comprises a first plurality of reservoirs for amino acid derivatives, a second plurality of reservoirs for peptide synthesis reagents, a column having a third plurality of separate column segments forming stacked, serially interconnected chambers for holding peptide synthesis polymeric resin supports, said separate column segments each having an axially extending bore with at least one mesh screen extending across said axially extending bore, said stacked chambers being formed between said mesh screens when said separate column segments are assembled in stacked relationship, each of said first plurality of amino acid derivative reservoirs and said second plurality of reagent reservoirs being connected through a separate controllable valve to said column, and means for supplying the amino acid derivatives and the reagents simultaneously to each of said separate column segments in said column.

2. The continuous flow peptide synthesizer of claim 1 in which said at least one mesh screen is attached to a peripheral ring and said axially extending bore has a portion of greater inside diameter than a remainder of said axially extending bore to form a ledge and said ring and at least mesh screen rests against said ledge.

3. The continuous flow peptide synthesizer of claim 1 in which said separate column segments each have one mesh screen, said stacked chambers being formed by said one mesh screen in adjacent separate column segments when said separate column segments are assembled in stacked relationship.

4. The continuous flow peptide synthesizer of claim 1 in which said separate column segments each have two mesh screens forming one of said stacked chambers between said two mesh screens.

5. The continuous flow peptide synthesizer of claim 1 in which said means for supplying the amino acid derivatives and the reagents comprises a source of an inert gas connected to an inlet of each of said first and second plurality of reservoirs, each of said reservoirs having an outlet connected through its separate controllable valve to said column.

6. The continuous flow peptide synthesizer of claim 5 in which the inert gas is helium.

7. A peptide synthesizer column, which comprises a housing configured to support a plurality of separate column segments in stacked relationship to form a serially interconnected plurality of stacked chambers, said separate column segments each having an axially extending bore with at least one mesh screen extending across said axially extending bore, said stacked chambers being formed between said mesh screens when said separate column segments are assembled in stacked relationship, said housing having at least one member movable along its length to allow said housing to support a variable number of said separate column segments in the stacked, serially connected relationship, said plurality of separate column segments including a separate inlet column segment, a separate outlet column segment and at least one additional separate column segment between said separate inlet column segment and said separate outlet column segment.

8. The peptide synthesizer column of claim 7 in which said separate column segments each have one mesh screen, said stacked chambers being formed by said one mesh screen in adjacent separate column segments when said separate column segments are assembled in stacked relationship.

9. The peptide synthesizer column of claim 7 in which said separate column segments each have two mesh screens forming one of said stacked chambers between said two mesh screens.

10. The peptide synthesizer column of claim 9 additionally comprising an insert member between adjacent ones of said separate column segments, said insert member having a central flow directing orifice communicating between the adjacent ones of said separate column segments.

11. The peptide synthesizer column of claim 7 in which said mesh screen is attached to a peripheral ring and said axially extending bore has a portion of greater inside diameter than a remainder of said axially extending bore to form a ledge and said ring and mesh screen rests against said ledge.

12. The peptide synthesizer column of claim 7 in which said axially extending bore has a portion of greater inside diameter than remainder of said axially extending bore, the remainder of said axially extending bore of a first one of said plurality of separate column segments fitting into the portion of greater inside diameter of a next adjacent second one of said plurality of separate column segments to form said stacked plurality of separate column segments.

13. The pepptide synthesizer column of claim 12 in which said greater diameter portion and said diameter of said bore have mating threads on a wall surrounding said bore.

14. The peptide synthesizer column of claim 7 in which said inlet separate column segment and said outlet separate column segment have an inlet passage extending through a wall of said inlet separate column segment and said outlet separate column segment to said axially extending bore.

15. A column segment, which comprises a cylinder having an axially extending bore with at least one mesh screen extending across said axially extending bore, said cylinder being configured to mate with a like cylinder in separate and stacking relationship to form serially interconnected, separate stacked chambers, said separate stacked chambers being formed between said mesh screens when said column segments are assembled in separate and stacked relationship.

16. The column segment of claim 15 in which said at least one mesh screen is attached to a peripheral ring and said axially extending bore has a portion of greater inside diameter than remainder of said axially extending bore to form a ledge and said ring and at least one mesh screen rests against said ledge.

17. The column segment of claim 15 in which said column segment has one mesh screen, the separate stacked chambers being formed by said one mesh screen in adjacent column segments when said column segments are assembled in separate and stacked relationship.

18. The column segment of claim 15 in which said column segment has two mesh screens forming one of said separate stacked chambers between said two mesh screens.

19. The column segment of claim 15 in which said axially extending bore has a portion of greater inside diameter than a remainder of said axially extending bore, the remainder of said axially extending bore of a first column segment fitting into the portion of greater inside diameter of a second column segment to assemble said first and second column segments in separate and stacked relationship.

20. The column segment of claim 19 in which said greater diameter portion and said remainder of said bore having mating threads on a wall surrounding said bore.

21. The column segment of claim 15 in which said cylinder has a feed passage extending through a wall of said cylinder to said axially extending bore.

22. A peptide synthesizer column comprising a plurality of the column segments of claim 15 in mating, separate and stacked relationship inside a tube having an axially extending passage configured to provide a close fit surrounding said plurality of column segments.

23. A continuous flow peptide synthesis process, which comprises providing a plurality of peptide synthesis polymeric resin support bodies separably stacked in serially interconnected relationship in a column, flowing peptide synthesis reagents for a plurality of synthesis steps which are identical for a plurality of resin support bodies simultaneously through the stacked bodies in the column, separating the stacked bodies for at least one synthesis step which is different for the resin support bodies, and flowing at least one different peptide synthesis reagent for each separated resin support body through the separated resin support bodies.

24. The continuous flow peptide synthesis process of claim 23 in which the at least one separated synthesis step is carried out after some of the plurality of identical synthesis steps, remaining ones of said plurality of identical synthesis steps being carried out simultaneously after said at least one separated synthesis step.

* * * * *